United States Patent
Dungy

(10) Patent No.: US 10,271,965 B2
(45) Date of Patent: Apr. 30, 2019

(54) PROSTHETIC GAP REFERENCES SYSTEM AND METHOD

(71) Applicant: Sterling Innovations, LLC, Scottsdale, AZ (US)

(72) Inventor: Danton S. Dungy, Scottsdale, AZ (US)

(73) Assignee: STERLING INNOVATIONS, LLC, Scottsdale, AZ (US)

( * ) Notice: Subject to any disclaimer, the term of this patent is extended or adjusted under 35 U.S.C. 154(b) by 278 days.

(21) Appl. No.: 15/151,380

(22) Filed: May 10, 2016

(65) Prior Publication Data

US 2017/0325868 A1  Nov. 16, 2017

(51) Int. Cl.
| | | |
|---|---|---|
| A61B 17/88 | (2006.01) | |
| A61F 2/30 | (2006.01) | |
| A61F 2/46 | (2006.01) | |
| A61B 17/16 | (2006.01) | |
| A61B 17/00 | (2006.01) | |
| A61F 2/38 | (2006.01) | |

(52) U.S. Cl.
CPC .. *A61F 2/4657* (2013.01); *A61B 2017/00707* (2013.01); *A61F 2/38* (2013.01); *A61F 2002/30387* (2013.01); *A61F 2002/4658* (2013.01); *A61F 2002/4668* (2013.01)

(58) Field of Classification Search
CPC ...... A61B 2017/00707; A61B 17/1675; A61B 2090/067; A61F 2/46; A61F 2/4657; A61F 2/468; A61F 2/4684; G01B 3/56
See application file for complete search history.

(56) References Cited

U.S. PATENT DOCUMENTS

| | | | |
|---|---|---|---|
| 4,211,228 A * | 7/1980 | Cloutier | ............. A61F 2/389 606/102 |
| 4,501,266 A | 2/1985 | McDaniel | |
| 4,566,448 A | 1/1986 | Rohr, Jr. | |
| 5,597,379 A | 1/1997 | Haines et al. | |
| 5,735,904 A | 4/1998 | Pappas | |
| 6,258,096 B1 | 7/2001 | Seki | |
| 6,991,653 B2 * | 1/2006 | White | ............. A61F 2/44 606/247 |
| 7,641,663 B2 | 1/2010 | Hodorek | |
| 7,704,253 B2 | 4/2010 | Bastian et al. | |
| (Continued) | | | |

OTHER PUBLICATIONS

Persona The Personalized Knee System surgical technique description, 2014.
(Continued)

*Primary Examiner* — Christian Sevilla
(74) *Attorney, Agent, or Firm* — Snell & Wilmer, L.L.P.

(57) ABSTRACT

Systems, kits, and methods are provided that may be used to assess a prosthetic gap in a resected joint, including an angular alignment of the resected bone surfaces in the joint. A system can comprise a reference spacer assembly comprising a spacer body with an elongated handle and one or two reference spacer plates. A kit can comprise a plurality of spacer bodies and reference spacer plates that can be selected and assembled by an operator to modularly produce assembled reference spacer devices having a range of different configurations. Methods for assessing a prosthetic gap, including a prosthetic gap dimension, a prosthetic gap symmetry, a tibial resection posterior slope, and a distal femoral resection angle, are also provided.

19 Claims, 14 Drawing Sheets

(56) References Cited

U.S. PATENT DOCUMENTS

| | | | |
|---|---|---|---|
| 8,257,360 B2 | 9/2012 | Richard et al. | |
| 8,529,573 B2 | 9/2013 | McAllister et al. | |
| 8,603,101 B2 * | 12/2013 | Claypool | A61F 2/389 |
| | | | 606/102 |
| 9,186,162 B2 * | 11/2015 | Wilkinson | A61B 17/17 |
| 9,358,126 B2 * | 6/2016 | Glerum | A61F 2/447 |
| 2013/0030538 A1 * | 1/2013 | Metzger | A61B 17/025 |
| | | | 623/20.3 |

OTHER PUBLICATIONS

Biomet Orthopedics Microplasty Total Knee Instrument surgical technique descriptions, 2010-2011.

Smith & Nephew Journey II BCS Bi-Cruciate Stabilized Knee System surgical technique description, 2013.

\* cited by examiner

PROSTHETIC GAP REFERENCES SYSTEM AND METHOD

FIELD

The present disclosure relates generally to devices, systems, and methods for implanting a prosthetic joint, and more particularly to devices, systems, and methods of assessing a prosthetic gap between a resected distal femur and a resected proximal tibia with reference to the opposing resected surfaces during a total knee replacement.

BACKGROUND

A variety of approaches are available for surgical preparation of a knee to receive a prosthetic joint in a total knee replacement procedure (also referred to as a total knee arthroplasty). Prior to replacing the knee joint with prosthetic components comprising a replacement knee joint, surgical cuts are generally made to resect portions of both the proximal tibia and distal femur. These cuts are made to prepare the tibia and femur to receive the prosthetic components. After these resections are performed, the prosthetic components can be attached and/or secured to the tibia and femur.

The desired orientation and/or position of the surgical cuts, and of the prosthetic components, can be determined pre-operatively and based, for example, on a mechanical axis running through an individual patient's leg. Once the desired locations of these cuts are determined pre-operatively, the surgeon can use various systems and methods known to a person of skill in the art to resect the tibia and femur.

Following resection of the tibial and femoral surfaces, it is important to confirm the dimension and symmetry of the prosthetic gap, which can include the extension gap and/or the flexion gap, as well as the angular alignment of the resected surfaces, to ensure proper selection and fit of the prosthetic components to be implanted. Failure to accurately assess the dimension and symmetry of the prosthetic gap and the angular alignment of the resected surfaces can produce misalignment of the implanted joint, resulting in post-recovery pain, joint instability poor joint function, and decreased implant longevity.

Therefore, devices, systems, and methods for assessing a prosthetic gap between a resected distal femur and a resected proximal tibia to assess proper implant fit and alignment prior to a trial reduction with prosthetic components are desirable.

SUMMARY

A prosthetic gap reference system is provided. A system may comprise a reference spacer support, a first reference spacer plate, and a plate retention device. A reference spacer support may comprise a spacer body and an elongated handle. The spacer body can comprise a first side and a second side substantially parallel to the first side, and the spacer body and the elongated handle can define a system axis. Each side of the spacer body can comprise a spacer body attachment feature. The first reference spacer plate can comprise a contact surface and an attachment feature configured to reversibly engage the spacer body attachment feature. The spacer body attachment feature can comprise a recessed open channel, and the reference spacer plate can comprise an elongate protrusion configured to slidably engage the spacer body attachment feature. A system can further comprise a plate retention device configured to be adjustably attached to the spacer body. A system can further comprise a second reference spacer plate. A reference spacer plate can be selected from a plurality of reference spacer plates, and the plurality of reference spacer plates can be configured to provide a range of predetermined anterior-posterior angles relative to the system axis when a reference spacer plate is engaged to the spacer body.

A kit for assessing a prosthetic gap between a resected distal femur and a resected proximal tibia, including a distal femoral resection angle and/or a tibial resection posterior slope, with reference to the opposing resected surfaces during a total knee replacement procedure, is provided. A kit may comprise a plurality of spacer bodies. Each of the plurality of spacer bodies can comprise a spacer body thickness and a spacer body attachment feature. The plurality of spacer bodies can be configured to provide a range of predetermined spacer body thicknesses. A kit can also comprise a plurality of reference spacer plates. Each of the plurality of reference spacer plates can comprise a reference spacer plate attachment feature configured to engage a spacer body attachment feature. The plurality of reference spacer plates can be configured to provide a range of predetermined anterior-posterior angles. A reference spacer plate and a spacer body can be selected by a user and manipulated into an assembled condition to produce a reference spacer assembly providing a predetermined references spacer assembly thickness and a predetermined posterior slope. Each of the plurality of spacer bodies can comprise an integrally attached elongated handle. In an embodiment, a kit can comprise a modular reference spacer assembly handle configured for removable attachment to each of the plurality of spacer bodies. A predetermined reference spacer assembly thickness can comprise a combined thickness of a spacer body and at least one reference spacer plate.

A method of assessing a prosthetic gap between a resected distal femur and a resected proximal tibia, including a tibial resection posterior slope and/or a distal femoral resection angle, with reference to the opposing resected surfaces during a total knee replacement procedure, is provided. A method may comprise selecting a spacer body from a plurality of spacer bodies. The spacer body can comprise a first side and a second side. A method can further comprise selecting a first reference spacer plate from a plurality of reference spacer plates and coupling the first reference spacer plate to one of the first side and the second side of the spacer body to produce a first assembled reference spacer system comprising a first predetermined reference spacer thickness. A method can further comprise contacting the first assembled reference spacer system to one of a resected distal femur and a resected proximal tibia in a prepared patient knee and assessing a prosthetic gap, including a tibial resection posterior slope and/or a distal femoral resection angle, relative to the first assembled reference spacer system. Assessing the prosthetic gap may determine at least one of a precise fit condition, a binding condition, an excessive free movement condition, a symmetry condition, an asymmetry condition, a tibial resection posterior slope congruity condition, a tibial resection posterior slope incongruity condition, a distal femoral resection angle congruity condition, and a distal femoral resection angle incongruity condition. A method can further comprise selecting a second reference spacer plate from the plurality of reference spacer plates and coupling the second reference spacer plate to the first spacer body. A method can further comprise substituting a second spacer body for the first spacer body. A method can further comprise substituting a third reference spacer plate for one of the first reference spacer plate and the second reference spacer plate.

BRIEF DESCRIPTION OF THE DRAWINGS

A more complete understanding may be derived by referring to the detailed description and claims when considered in connection with the Figures, wherein like reference numbers refer to similar elements throughout the Figures, and wherein:

DETAILED DESCRIPTION

Figure 1A:
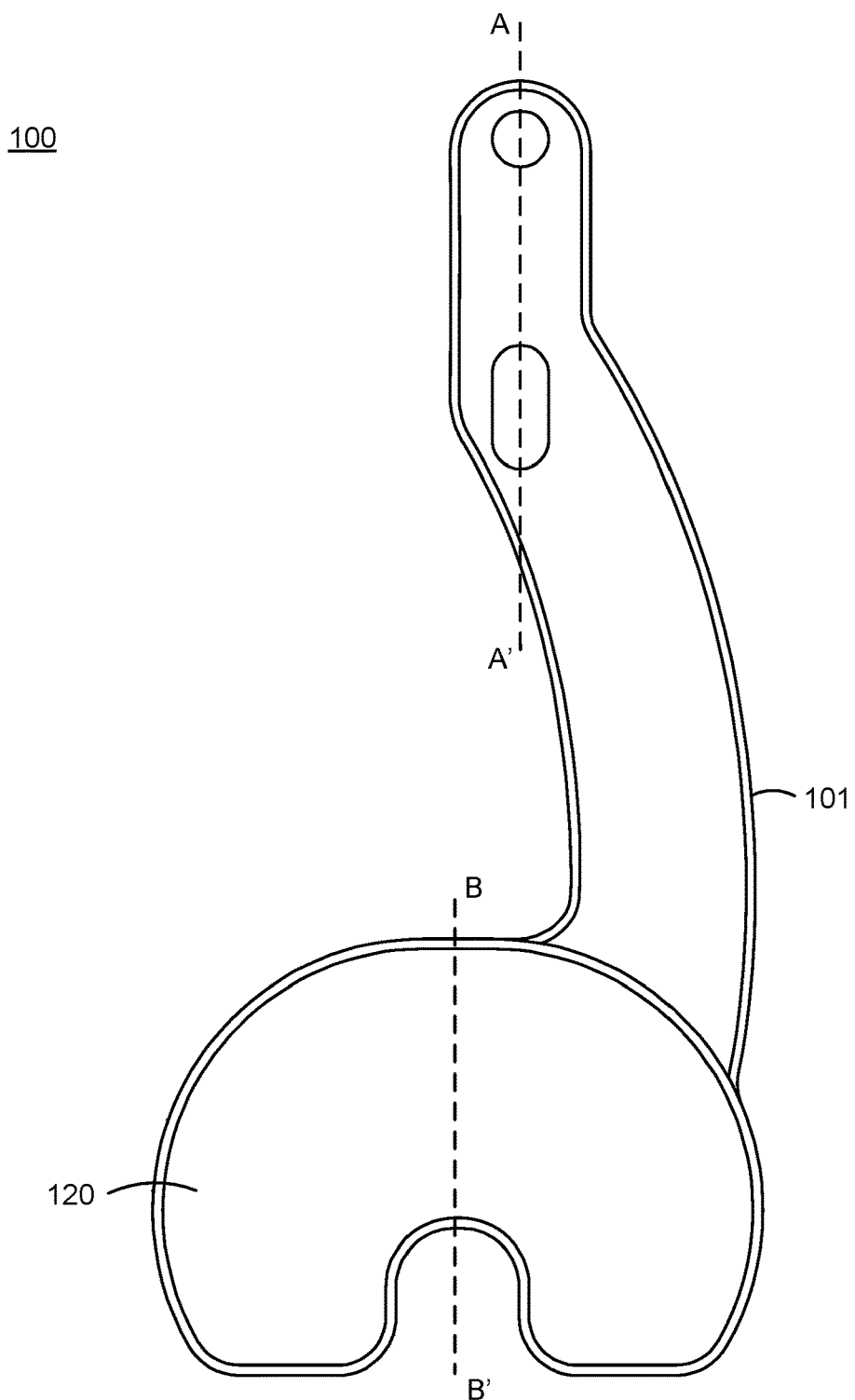
FIG. 1A illustrates a top view of a system according to various embodiments of the present disclosure.

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Furthermore, any reference to singular includes plural embodiments, and any reference to more than one component may include a singular embodiment.

Various systems, kits, and methods are provided in this disclosure. In the detailed description herein, references to "various embodiments," "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to include such feature, structure, or characteristic in connection with other embodiments whether or not explicitly described. After reading the description, it will be apparent to one skilled in the relevant art(s) how to implement the disclosure in alternative embodiments.

Systems, kits, and methods for assessing a prosthetic gap between a resected distal femur and/or a resected posterior femur and a resected proximal tibia, including a tibial resection posterior slope and/or a distal femoral resection angle, with reference to the opposing resected surfaces during a total knee arthroplasty procedure, are disclosed according to various embodiments. Although the present disclosure describes systems, kits, and methods in relation to a total knee arthroplasty procedure, a person of skill in the art will appreciate that the configuration of the various devices, device components, and methods described herein may be readily modified or adapted for application in other joints or portions of a patient's body, and such other applications are contemplated within the scope of the present disclosure.

In various embodiments, a prosthetic gap reference system is provided which can be used for verifying a prosthetic gap dimension, symmetry, and/or an angular alignment of a resected tibial surface plane and/or a resected distal femoral surface plane, during an orthopedic surgical procedure. As used herein, the term "prosthetic gap reference system" is a broad term, and includes, without limitation, devices which can be used alone or in conjunction with an orthopedic fixture or fixtures to assess a relative position of one or more surgical devices or anatomical structures, and can encompass any of the embodiments shown in the drawings and described herein. For example, FIGS. 1A-1E show an embodiment of a prosthetic gap reference system 100. Prosthetic gap reference system 100 can comprise a compact, generally hand-held and/or portable system for use in assessing a prosthetic gap dimension, symmetry, and/or an angular alignment of a resected plane of a bone. Reference system 100, as described herein, can be used alone or in conjunction with other devices, components, and/or systems, such as resection jigs, alignment systems, prosthetic device components, etc.

As used herein, the term "prosthetic gap" means the surgically created space between a patient's bones required to accommodate implantation of a prosthetic device, such as an artificial knee. The term "prosthetic gap" can be used to refer to an actual prosthetic gap, or a planned prosthetic gap that will have a desired configuration following the resection steps required to achieve the actual prosthetic gap. As used herein, the term "prosthetic gap" can include concepts such as a prosthetic gap dimension, prosthetic gap symmetry, and resected surface angular alignment. As used herein, the term "prosthetic gap" and the various concepts included therein can be evaluated with respect to both an extension gap and a flexion gap in a total knee replacement procedure.

As used herein, the term "prosthetic gap dimension" can include the distance between two adjacent resected bone surfaces. For example, implantation of an artificial knee may require resection of a patient's proximal tibia and femur, with removal of a sufficient amount of bone tissue to permit replacement by a prosthetic joint having a particular dimension in the space between the resected bones. Resection of a femur can include resection of the distal femur as well as resection of the posterior femoral condyles, producing a resected distal femoral surface and a resected posterior femoral surface, respectively.

As used herein, the term "prosthetic gap symmetry" can include symmetry of the resected surfaces from an anterior-posterior perspective. For example, a prosthetic gap can be symmetrical (i.e., rectangular or balanced) or asymmetrical (i.e., trapezoidal or imbalanced) with respect to the alignment of the resected surfaces evaluated from an anterior-posterior perspective.

As used herein, the term "resected surface angular alignment" can include, for example, a distal femoral resection angle and/or a tibial resection posterior slope in an anterior-posterior direction.

In various embodiments, a prosthetic gap reference system may be used in a joint resection and prosthetic joint implantation procedure to assess a prosthetic gap, including a prosthetic gap dimension and a prosthetic gap symmetry, between one or more resected surfaces of the bones in a joint during a surgical procedure to implant a prosthetic joint. Likewise, a prosthetic gap reference system used to assess a prosthetic gap may be used to assess the resected surface angular alignment of the bones in a joint during a surgical procedure. Use of a reference system in accordance with various embodiments of the present disclosure may facilitate accurate preparation of a surgical site to receive a prosthetic joint and/or selection of an appropriately configured prosthetic joint for the prosthetic gap in a resected joint.

In various embodiments, a prosthetic gap reference system can comprise a reference spacer support, one or more reference spacer plates, and one or more plate retention devices. With reference now to FIGS. 1A-1E, a prosthetic gap reference system 100 in accordance with various embodiments is illustrated. Reference system 100 can comprise reference spacer support 101. Reference spacer support 101 can comprise a spacer body 102 and an elongated handle 103. Spacer body 102 can have a reniform (i.e., kidney-shaped) profile from a top or bottom perspective, with the spacer body configured to approximate the size and shape of a resected femur and/or tibia, with a posterior concavity configured to accommodate posteriorly located soft tissues during use of the reference system. In various embodiments, reference spacer support 101 can have a unitary construction, with spacer body 102 and elongated handle 103 being integrally attached, as illustrated in FIGS. 1A-1E.

Alternatively, in various embodiments, a reference spacer support can be modular and comprise a spacer body that can be removably attached to an elongated handle by a connection mechanism, such as by a threaded fit, a snap fit, or other interference fit connection mechanism. In this manner, a plurality of spacer bodies having a plurality of spacer body thicknesses may be interchangeably connected to a single elongated handle. Any connection mechanism now known to or hereinafter devised by a person of skill in the art may be included within the scope of the present disclosure.

In various embodiments, a reference spacer support can comprise an offset handle configuration in which the elongated handle is offset relative to the spacer body in a top or bottom perspective. For example and as shown in FIG. 1A, an axis A-A' of a proximal end of elongated handle 103 is offset from midline B-B' of spacer body 102, with the balance of the elongated handle 103 connecting the proximal end to spacer body 102 further offset from midline B-B'. In various embodiments, the entirety of elongated handle 103 can be offset relative to the spacer body, and midline B-B' may not intersect any portion of elongated handle 103. In various embodiments, an offset handle configuration may provide certain functional benefits to use of a reference system, including increased visibility of the interior of a joint, reduced interference with anatomical features such as a patellar tendon, or retraction of anatomical features such as a patellar tendon laterally and out of the viewing and working area. Spacer body 102 is described in greater detail below.

In various embodiments, a reference system can comprise one or more reference spacer plates. A reference spacer plate can be removably attached to a surface of a spacer body. A reference spacer plate may be selected by an operator from a plurality of different reference spacer plates, each reference spacer plate having a reniform profile that substantially corresponds to the spacer body profile, while having a range of different configurations relative to the side profile (see, e.g., FIGS. 4 and 5). For example, reference system 100 can comprise a first reference spacer plate 120. First reference spacer plate 120 can be removably attached to a first surface 104 of spacer body 102. In various embodiments, a reference system 100 can further comprise a second reference spacer plate 130. Second reference spacer plate 130 can be removably attached to a second surface 105 of spacer body 102 opposite first surface 104. First surface 104 can define a first plane and second surface 105 can define a second plane, and spacer body 102 can further comprise a thickness $t_1$ defined by the distance between the first and second planes defined by first surface 104 and second surface 105. In various embodiments, the first plane defined by first surface 104 and the second plane defined by second surface 105 may be coplanar and parallel to an axis C-C' (FIG. 1B) defined by reference spacer support 101 and/or spacer body 102. In various embodiments, a spacer body and/or a reference spacer support may be bilaterally symmetrical about axis C-C', such that the spacer body or reference spacer support may be reversibly used, for example, for both a right knee and a left knee, as further described herein.

In various embodiments, a spacer body can comprise one or more attachment features. An attachment feature can be configured to provide for removable attachment of a reference spacer plate. A spacer body can include an attachment feature on a single surface of the spacer body, or a spacer body can include attachment feature on a first and a second surface of the spacer body. An attachment feature can have any of a variety of configurations now known to or hereinafter devised by a person of skill in the art, such as a t-channel configuration. For example, and with reference now also to FIG. 2 and FIGS. 3A and 3B, spacer body 102 comprises a first t-channel 106 recessed in and transecting first surface 104 and a second t-channel 107 recessed in and transecting second surface 105. Each t-channel can be open at either end of the channel and configured to slidably receive a complementary t-shaped protrusion configured to provide a clearance fit in the channel, such as t-shaped protrusions 121 and 131 of reference spacer plates 120 and 130, respectively, from either side of the spacer body. In various embodiments, a t-channel may comprise an asymmetric cross-section, for example, with the two "arms" of the "t" having different dimensions. An asymmetric protrusion cross-section may be used to ensure that a reference plate may only be inserted in the proper orientation, as described in greater detail below.

In various embodiments, a reference system can comprise a plate retention device. A plate retention device can be configured to secure a reference spacer plate to a reference spacer support, for example, with an interference fit. In various embodiments, a plate retention device can be removably and/or adjustably attached to a spacer body. For example, and with reference briefly to FIG. 1C, reference system 100 comprises a first plate retention device 108 removably attached to spacer body 102 at first surface 104 and a second plate retention device 109 removably attached to spacer body 102 at second surface 105. In various embodiments, a plate retention device such as first plate retention device 108 and second plate retention device 109 can comprise a ball plunger, as described in greater detail below. However, other retention mechanisms now known to or hereinafter devised by a person of skill in the art may be included within the scope of the present disclosure.

Figure 2:
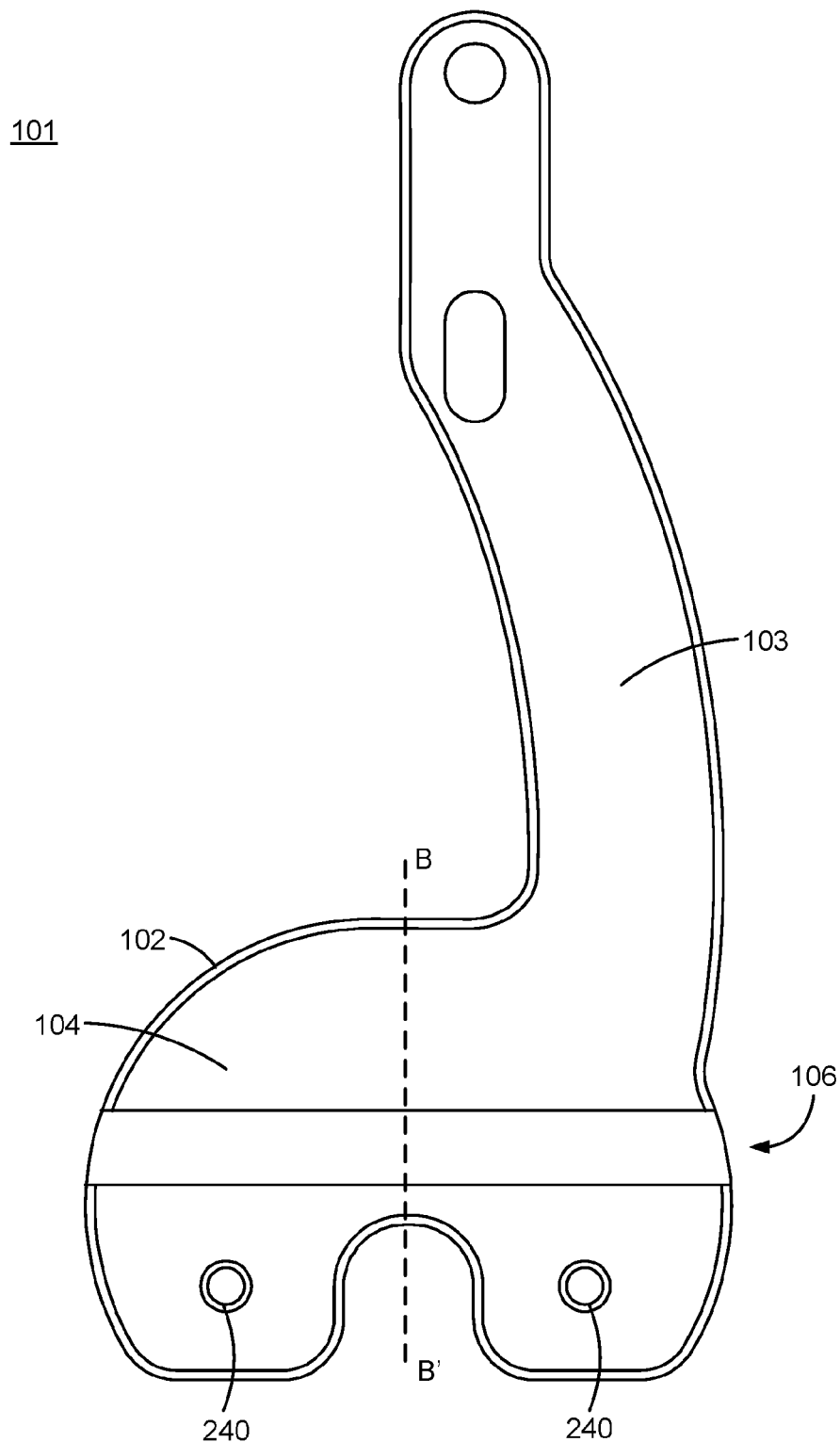
FIG. 2 illustrates a top view of a reference spacer support according to various embodiments of the present disclosure.
Figure 3A:
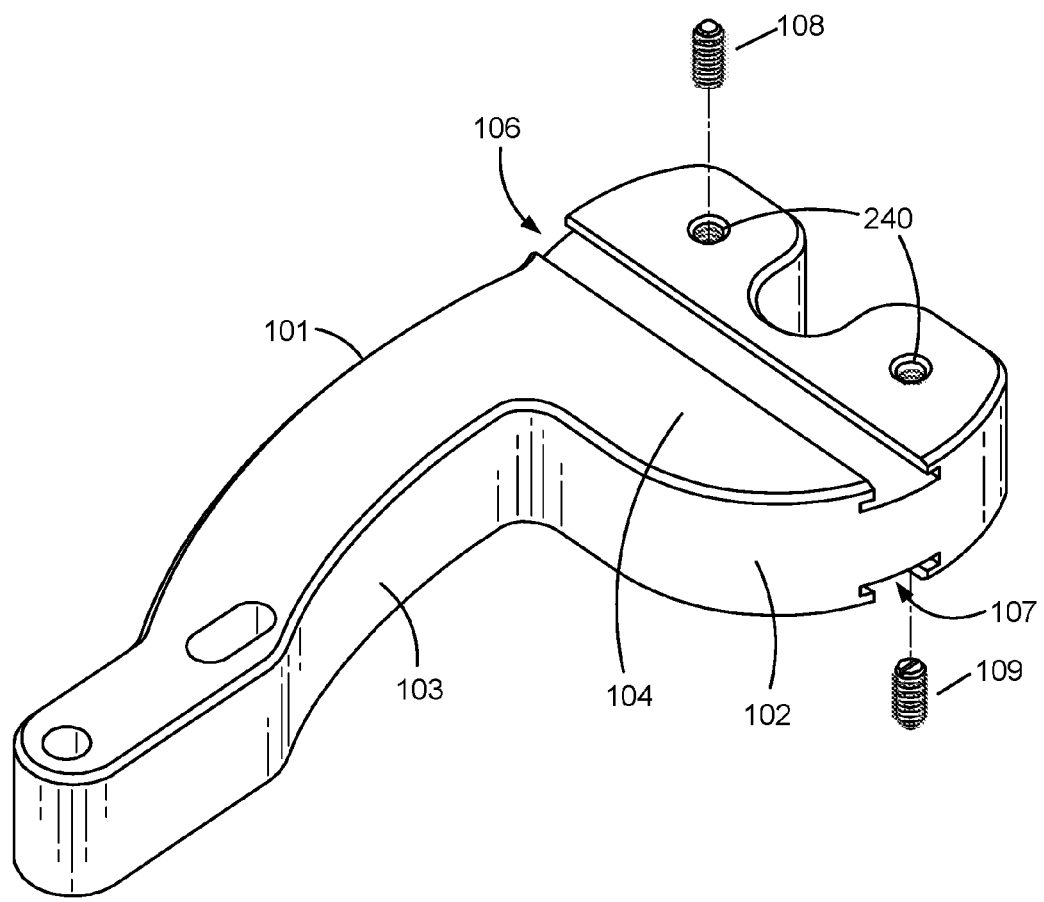
FIGS. 3A and 3B illustrate exploded perspective views of a reference spacer support and plate retention devices according to various embodiments of the present disclosure.
Figure 3B:
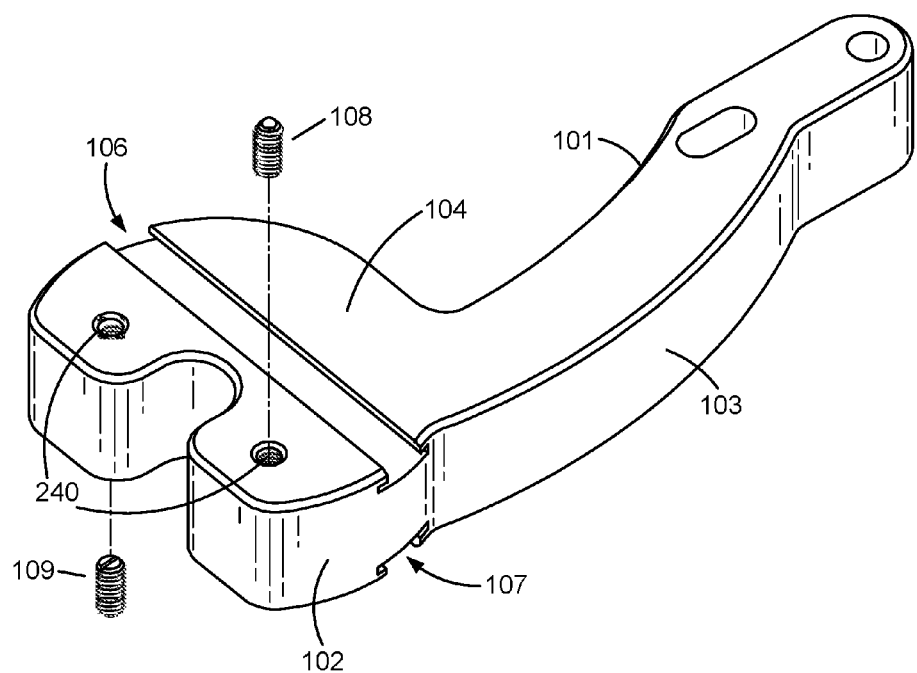

With continued reference to FIG. 2 and FIGS. 3A and 3B, various views of reference spacer support 101 with the reference spacer plates removed are illustrated. As shown in FIG. 2, first t-channel 106 transects first surface 104 of spacer body 102 in an orientation substantially perpendicular to midline B-B' of spacer body 102 and is open at either end of channel 106. However, other configurations of a channel-type attachment feature are possible, including a channel configuration that only partially transects a spacer body surface and only permits insertion of a reference plate having a complementary plate attachment feature from one side of a spacer body.

Other attachment feature configurations or coupling mechanisms for attaching a reference spacer plate to a spacer body are possible within the scope of the present disclosure. For example, a coupling mechanism can comprise other configurations suitable to provide a secure transition fit or interference fit that permits rapid coupling and decoupling by an operator without tools, such as a keyhole attachment mechanism (e.g., with insertion in a first direction and sliding movement in a second direction to secure), a twist-lock style coupling mechanism (e.g., a socket configured to receive a lugged shaft that may be secured with a partial rotation), a combination magnetic and mechanical attachment mechanism (e.g., a magnetic coupling force with a mechanically keyed alignment), and the like. A coupling mechanism can also comprise a clearance fit attachment or other method of mating and aligning a spacer body and a reference spacer plate, followed by securing the reference spacer plate to the spacer body with a bolt, pin, or other fastener used as a plate retention device that may or may not require a tool to secure.

A spacer body can comprise one or more apertures configured to receive a plate retention device. For example, spacer body 102 comprises apertures 240 configured to receive plate retention devices 108 and 109. In the illustrated embodiment, each aperture 240 comprises a threaded bore, and each plate retention device 108 and 109 comprises a ball plunger configured to threadedly engage aperture 240. Each ball plunger can comprise an externally threaded cylinder that is closed at one end and open at an opposite end, with the open end comprising a moveable ball press-fit into the open end and urged toward the open end by a spring member contained within the cylinder. Each ball plunger can comprise a tool interface at the closed end and/or at the open end, such as the flat head screwdriver interface illustrated. Each ball plunger can be removably and adjustably inserted into spacer body 102 to provide an interference fit with a reference spacer plate, such as at a corresponding feature located on a bottom surface of a reference spacer plate at a location configured to provide alignment of the reference spacer plate with spacer body 102, as described in greater detail below. With reference briefly back to FIG. 1C, each ball plunger used as plate retention devices 108 and 109 can be adjustably inserted into the corresponding apertures in spacer body 102 such that the moveable ball protrudes or emerges from the plane of the spacer body surface and can engage the bottom surface of a reference spacer plate to provide an interference fit.

Figure 1B:
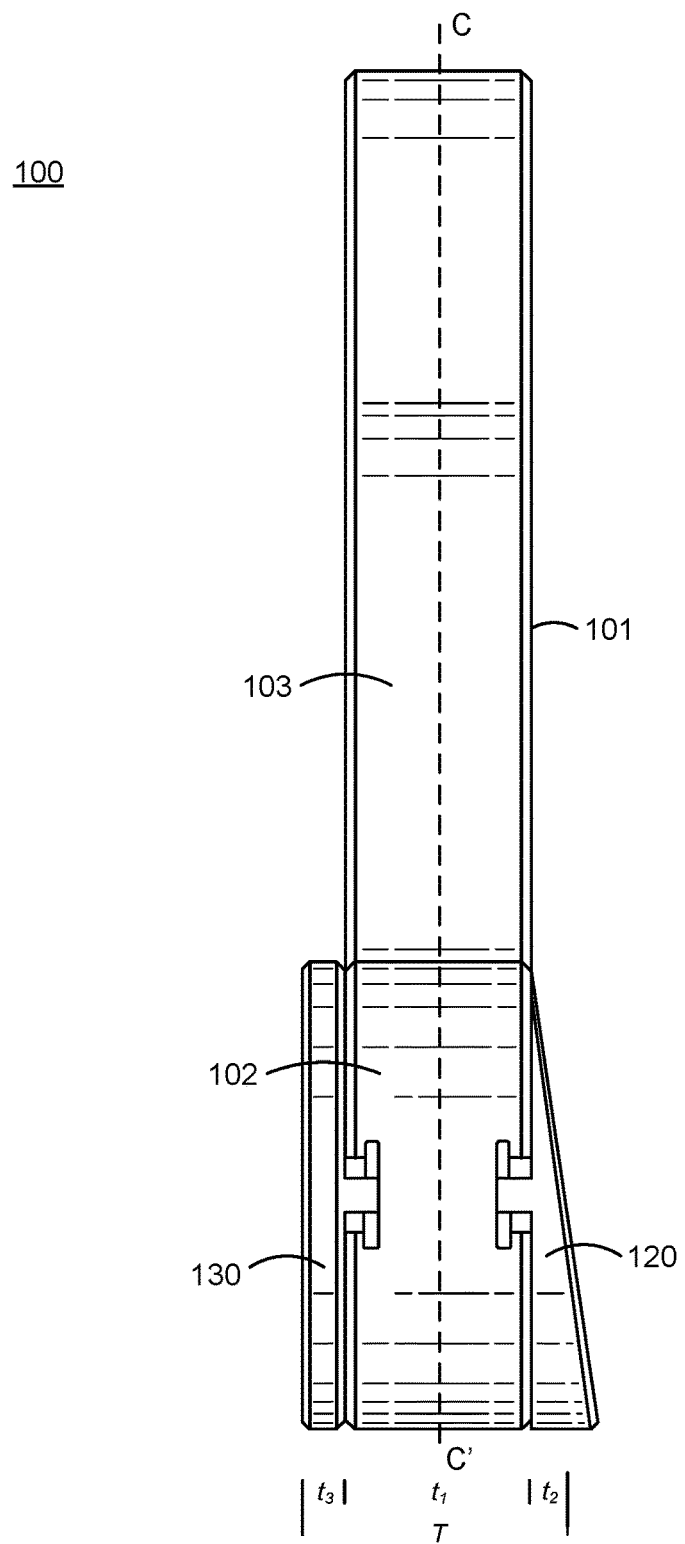
FIG. 1B illustrates a side view of a system according to various embodiments of the present disclosure.
Figure 1C:
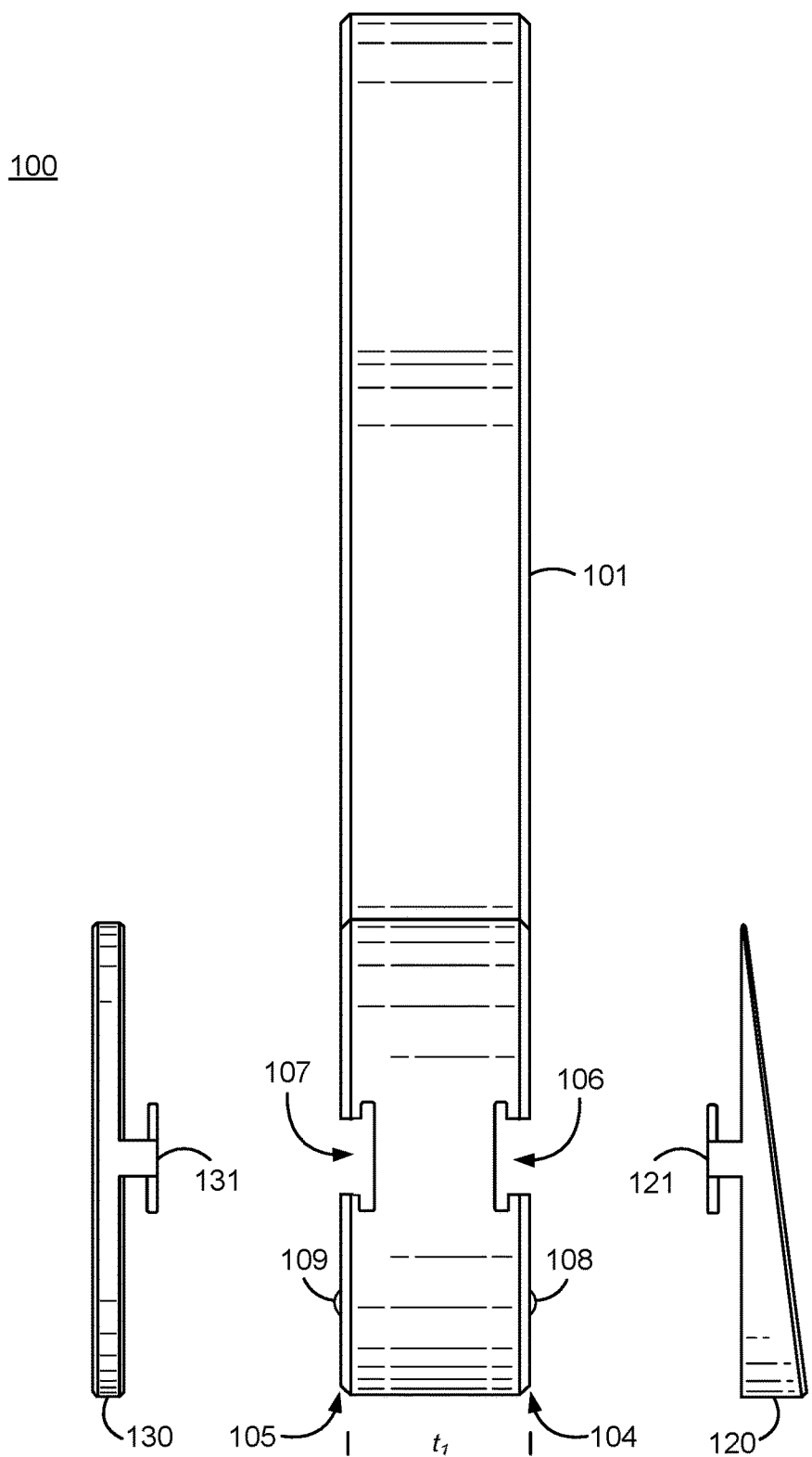
FIG. 1C illustrates a partially exploded side view of a system according to various embodiments of the present disclosure.
Figure 1D:
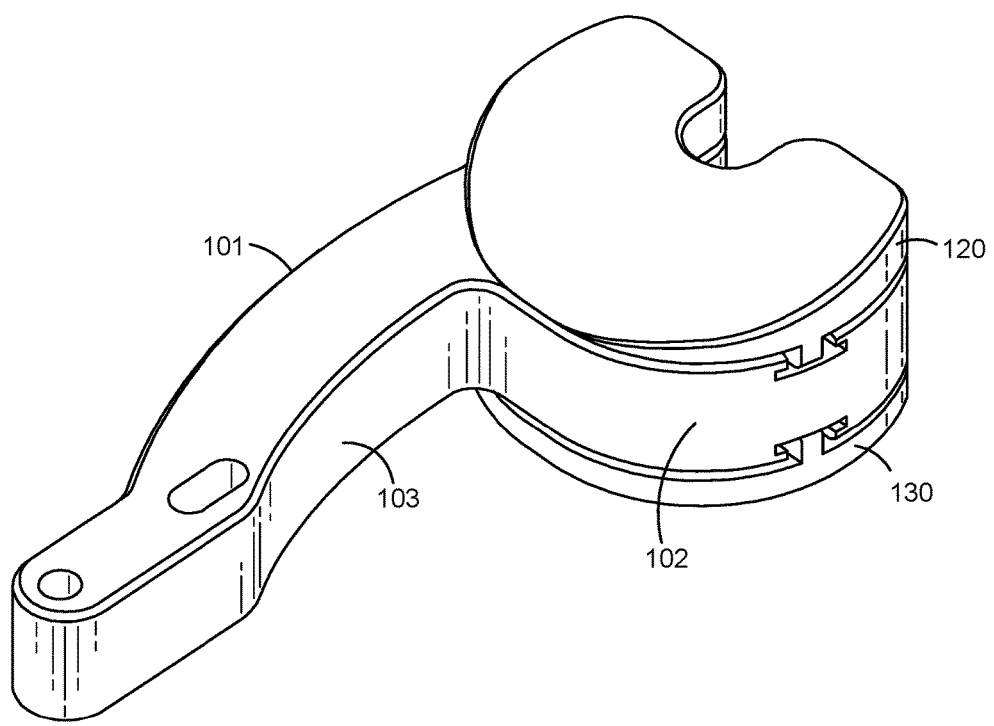
FIGS. 1D and 1E illustrate a perspective views of a system according to various embodiments of the present disclosure.
Figure 1E:
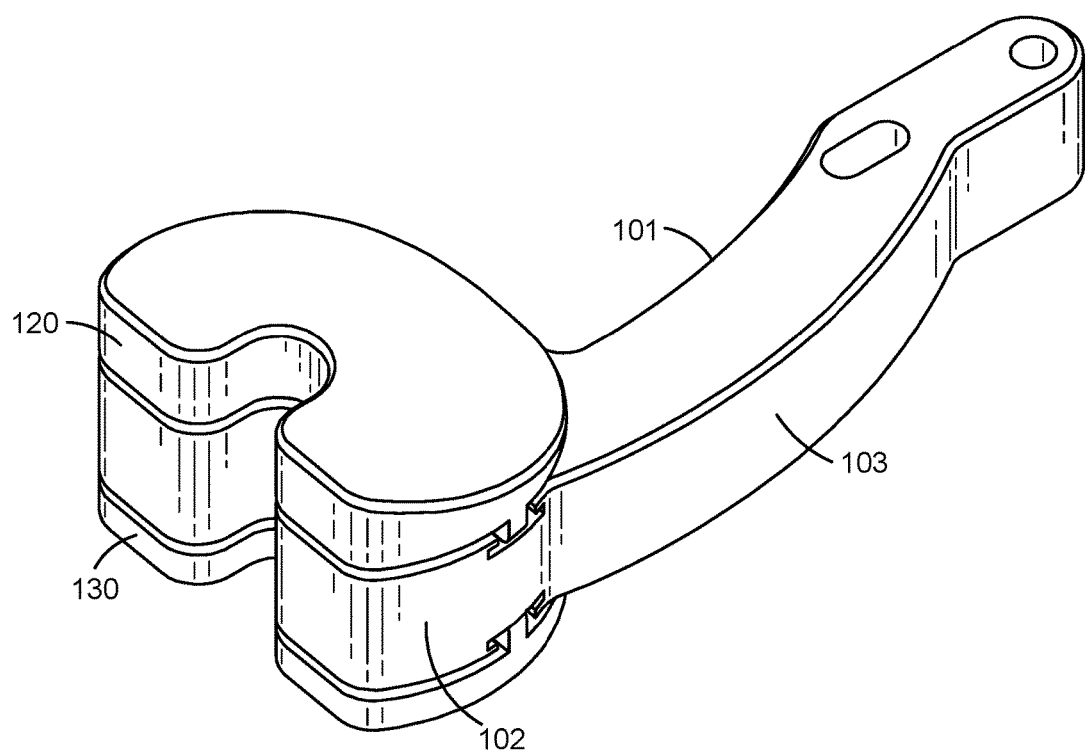
Figure 4:
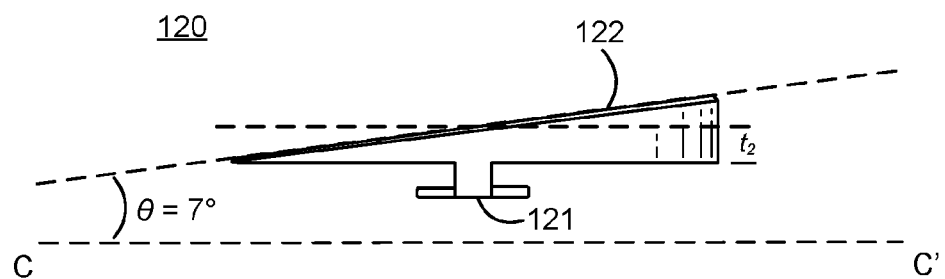
FIGS. 4 and 5 illustrate side views of reference spacer plates according to various embodiments of the present disclosure.
Figure 5:
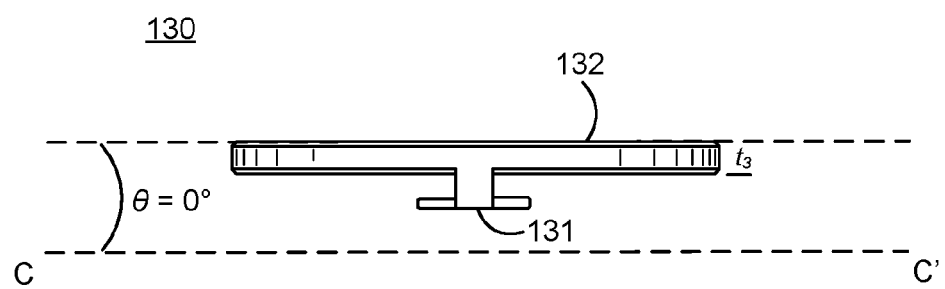
Figure 6A:
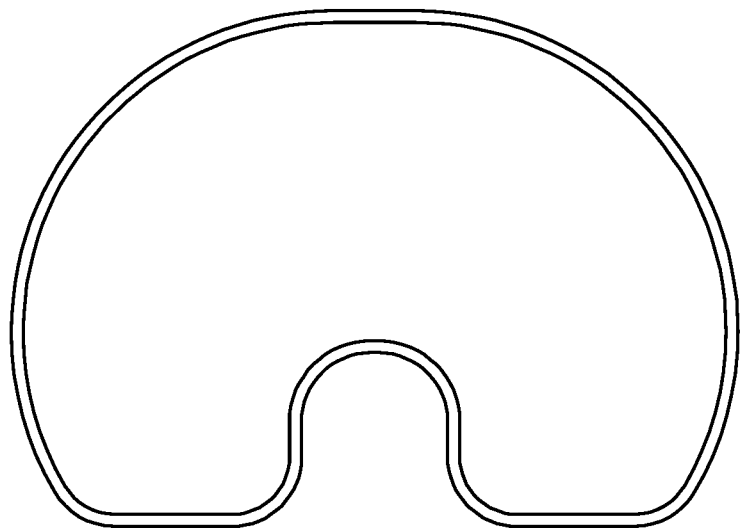
FIGS. 6A-6C illustrate views of a reference spacer plate according to various embodiments of the present disclosure.
Figure 6B:
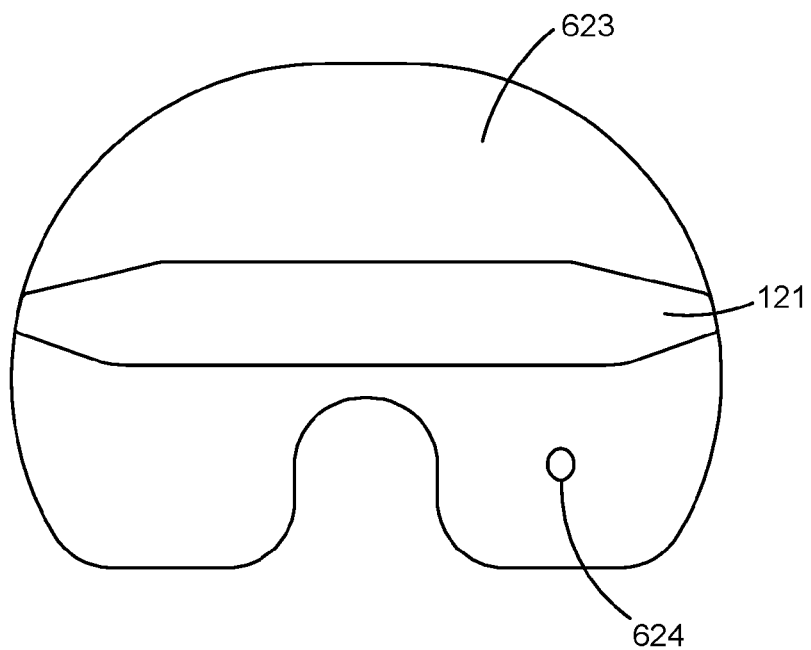
Figure 6C:
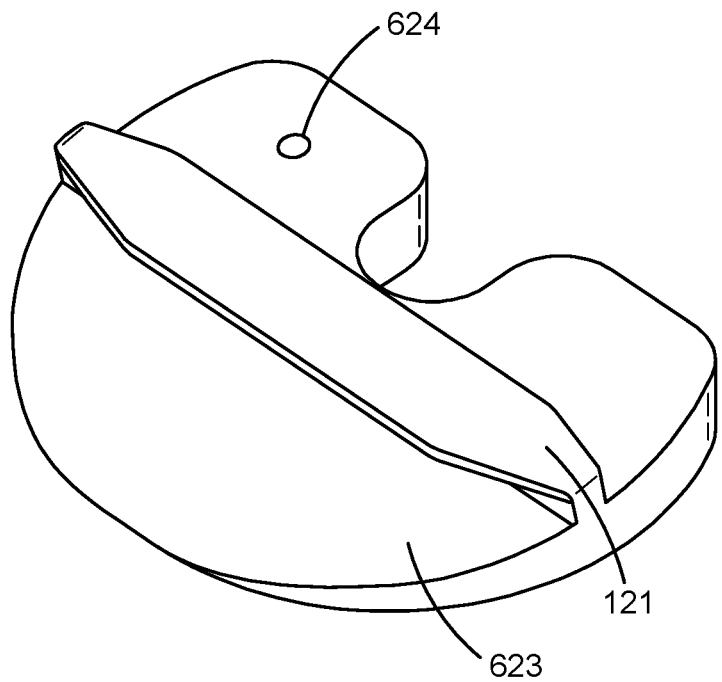

With reference now to FIGS. 4, 5, and 6A-6C, as well as to FIGS. 1B and 1C, further details of reference spacer plates in accordance with various embodiments are described and illustrated. In various embodiments, a reference spacer plate comprises a contact surface configured to contact a resected bone structure and defining a contact surface plane, and an attachment surface on an opposite side of the reference spacer plate. The contact surface plane can define an anterior-posterior angle θ relative to axis C-C' (see also FIG. 1B) of a reference spacer support when the reference spacer plate is assembled to the reference spacer support. FIG. 4 illustrates a side view of reference spacer plate 120, and FIG. 5 illustrates a side view of reference spacer plate 130. As shown in FIG. 4, reference spacer plate 120 comprises contact surface 122. Contact surface 122 defines a contact surface plane sloped in an anterior-posterior direction relative to a plane defined by axis C-C'. The anterior-posterior angle θ between the contact surface plane and the plane defined by axis C-C' for reference spacer plate 120 is 7°. Reference spacer 130, illustrated in FIG. 5, comprises contact surface 132 defining a contact surface plane parallel to axis C-C' (anterior-posterior angle θ is 0°).

In various embodiments, a reference system kit can comprise a plurality of reference spacer plates offering a range of anterior-posterior angles. A range of anterior-posterior angles can comprise various incremental differences between angles, for example, 0°, 3°, and 7°; 0°, 2°, 5°, and 7°; etc. Any suitable number of reference spacer plates offering any suitable range of anterior-posterior angles can be included in a reference system kit in accordance with various embodiments. A reference spacer plate may be selected by an operator from the plurality of reference spacer plates, for example, based on an actual or planned anterior-posterior slope of a resected tibia. The selected reference spacer plate can then be assembled to the reference spacer support, and the assembled reference system used to assess the prosthetic gap between two resected surfaces.

In various embodiments, a reference spacer plate comprises a reference spacer plate thickness. A reference spacer plate thickness can comprise a dimension between a point on the contact surface of the reference spacer plate and a point on a plane defined by the attachment surface and/or a plane defined by a surface of a spacer body of a reference spacer support. In various embodiments, a reference spacer plate thickness may be determined at a midpoint of the plate in an anterior-posterior dimension. For example and with reference to FIG. 4, a midpoint of spacer plate 120 is substantially aligned with the centerline of t-shaped protrusion 121, and reference spacer plate thickness $t_2$ is defined as the distance between a point on contact surface 122 at the midpoint and the plane defined by the attachment surface. Similarly, and with reference to FIG. 5, reference spacer plate thickness $t_3$ is defined as the distance between a point on contact surface 132 and the plane defined by the attachment surface of plate 130.

In various embodiments, a reference spacer plate can be configured with a predetermined thickness. Moreover, each spacer plate in a plurality of spacer plates comprising range of anterior-posterior angles can be configured to provide a substantially uniform reference spacer plate thickness, for example, about 3 mm, regardless of the anterior-posterior angle of the contact surface of the plate. In this manner, reference spacer plates having different anterior-posterior angles can be interchanged from an assembled reference system without changing the overall reference system thickness T (e.g, $T=t_1+t_2+t_3$). In various embodiments, a plurality of spacer plates comprising a range of thicknesses may also be provided. For example, a plurality of plates can include a plurality of 0° plates having a range of different thickness, such as about 1 mm, about 2 mm, about 3 mm, about 4 mm, and about 5 mm. Other ranges and increments, including increments with non-integer values, such as about 1.5 mm, about 2.5 mm, and the like, are also possible and within the scope of the present disclosure.

In various embodiments, a kit can comprise a plurality of reference spacer supports or spacer bodies and a plurality reference spacer plates that may be modularly assembled to provide an assembled reference system having an operator selected, predetermined reference system thickness and anterior-posterior contact surface angles. In various embodiments, a kit can comprise a plurality of reference spacer supports or spacer bodies having a range different spacer body thickness, such as about 11 mm, about 13 mm, about 15 mm, about 17, about 19 mm, and about 21 mm. A kit can comprise more or fewer components offering different size ranges and different increments between consecutive components in the range, such as from 2-10 components with increments of about 0.5 mm, or about 1 mm, or about 2 mm, or about 3 mm, and the like. Likewise, a kit can comprise a plurality of reference spacer plates providing a range of reference spacer plate thicknesses and/or a range of anterior-posterior contact surface angles, as described above. In various embodiments, each component may be permanently marked with information corresponding to the thickness and/or the contact surface angle of the component to enable the operator to selectively assemble a reference system providing predetermined overall thickness and contact surface anterior-posterior slope parameters, or to allow the operator to ascertain the overall assembled reference system thickness and contact surface anterior-posterior slope parameters in an assembled reference system.

An attachment surface of a reference spacer plate can comprise a plate attachment feature configured to engage a complementary spacer body attachment feature. A plate attachment feature can comprise a t-shaped protrusion configured to slidably engage a complementary t-channel with a clearance fit, such as t-shaped protrusions 121 and 131 of reference spacer plates 120 and 130, respectively. In various embodiments, a reference spacer plate can be attached to a spacer body by an operator without tools. A plate attachment feature and corresponding spacer body attachment feature can be configured to provide engagement of the reference plate to the spacer body in a specific orientation. For example, t-shaped protrusions 121 and 131 can comprise an asymmetric cross-section, with the posterior arms of the protrusions having a greater thickness than the anterior arms of the protrusions, thereby prohibiting engagement of the reference spacer plate in an improper orientation wherein the outer profile of the reference spacer plate is not aligned with that of the spacer body. As mentioned above, other attachment feature configurations and coupling mechanisms are possible, and a person of skill in the art will appreciate that a plate attachment feature can have any of a variety of configurations suitable to provide attachment to a corresponding feature of a spacer body.

In various embodiments, an attachment surface of a reference spacer plate can comprise a retention device reference feature configured to receive or otherwise contact or reference a plate retention device. A retention device reference feature can comprise, for example, a depression in an attachment surface of a reference spacer plate. The depression may be located to correspond to the location of a plate retention device in an assembled reference system when a reference spacer plate is attached to and properly aligned with a spacer body of a reference spacer support, and may be further configured to receive a portion of a plate retention device, with the depression serving as a mechanical detent and providing an interference fit between the reference spacer plate and the reference spacer support with the plate retention device. For example, and with reference to FIGS. 6B and 6C, attachment surface 623 of reference spacer plate 120 is illustrated. Reference spacer plate 120 comprises depression 624 machined in attachment surface 122. The location of depression 123 corresponds to the location of a ball plunger, and depression 123 is configured to partially receive the ball of a ball plunger, thereby providing an interference fit and retention of the reference spacer plate in the assembled reference system.

In accordance with various embodiments, a reference system need not comprise adjustable components. Rather, for the sake of simplicity, ease of use, and ease of cleaning, maintenance, and reuse, a system can comprise modular reference spacer support and reference spacer plate components that may be assembled to one another to provide fixed relative positions that cannot be adjusted (i.e., the system is non-adjustable) except for disassembly and reassembly, which concepts are not included within the meaning of adjustment. Instead, assessment of different prosthetic gap configurations is achieved by a procedure of disassembly of an assembled system and reassembly of the system with a component providing a different thickness and/or anterior-posterior angle (e.g., tibial resection posterior slope or distal femoral resection angle), as described in greater detail below.

A reference system in accordance with various embodiments can comprise components manufactured from any suitable material. For example, a reference spacer body, reference spacer support, and/or a reference spacer plate may be manufactured from a metal material such as stainless steel, aluminum, titanium, or any other metal or metal alloy suitable for use in a surgical setting. Alternatively, in various embodiments, a reference system component such as a reference spacer plate can comprise a polymeric material, while the other components of the system such as the reference spacer body or the reference spacer support can comprise a metal material. A polymeric material component may be constructed of a thermoplastic polymer such as polyether ether ketone, polyetherimide, or other similar polymer materials, such as polycarbonate, polystyrene, ABS, acrylics, polyimide, polyethersulfone, polyphenylsulfone, polymethylmethacrylate, or any other bio-compatible, injection-moldable polymer. In various other embodiments of a system, the reference spacer plates and the reference spacer support may comprise polymer materials.

Figure 7:
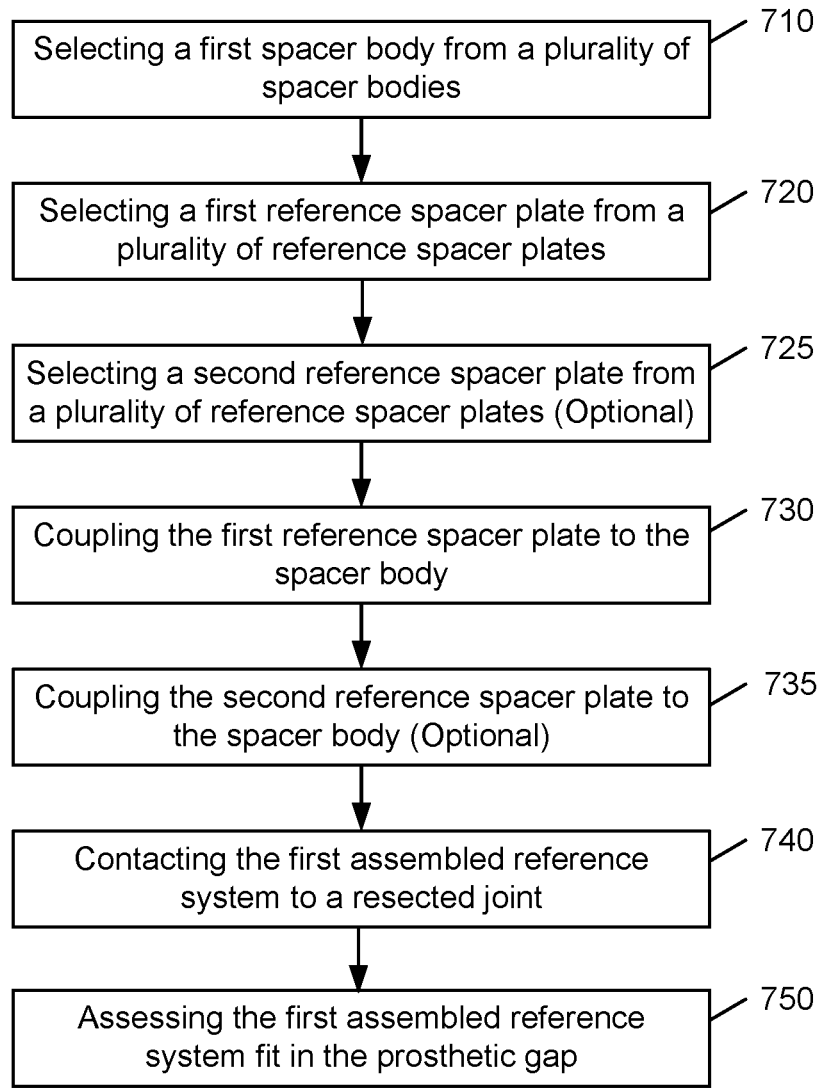
FIG. 7 illustrates a process for establishing a distal femoral resection position in a total knee arthroplasty procedure according to various embodiments of the present disclosure.

With reference now to FIG. 7, a method 700 of assessing a prosthetic gap can comprise the steps of: selecting a first spacer body from a plurality of spacer bodies (step 710); selecting a first reference spacer plate from a plurality of reference spacer plates (step 720); coupling the first reference spacer plate to the spacer body (step 730); contacting the first assembled reference system to a resected joint (step 740); and assessing the first assembled reference system fit in the prosthetic gap (step 750). A method 700 can further comprise an optional step of selecting a second reference spacer plate (725) and coupling the second reference spacer plate to the spacer body (step 735).

In various embodiments, method 700 comprises selecting a first spacer body from a plurality of spacer bodies (step 710). In various embodiments, selecting a first spacer body can comprise selecting a first spacer body and assembling the first spacer body to an elongated handle in various embodiments comprising a modular reference spacer support, or selecting first spacer body can comprise selecting a first reference spacer support comprising a spacer body integrally attached to an elongated handle. The first spacer body may be selected to provide a predetermined spacer body thickness and/or a predetermined assembled reference system thickness, based on a planned or estimated prosthetic gap dimension of a resected joint and accounting for the anticipated reference spacer plate thickness of a first and/or second reference spacer plate to be coupled to the first spacer body in subsequent steps, described below.

Method 700 can further comprise selecting a first reference spacer plate from a plurality of reference spacer plates (step 720). Method 700 can further optionally comprise selecting a second reference spacer plate from the plurality of reference spacer plates (step 725). In various embodiments, a surface of a spacer body can comprise a contact surface of an assembled reference system, and a reference system need not comprise a second reference spacer plate. A first and/or second reference spacer plate can be selected based on at least one of a reference spacer plate thickness and a reference spacer plate anterior-posterior angle. The reference spacer plate thickness and reference spacer plate anterior-posterior angle can be selected to produce a predetermined assembled reference system thickness, in combination with a spacer body to which the reference spacer plates are attached, and/or an anterior-posterior angle. As for selection of the spacer body, a first and/or second reference spacer plate may be selected based on a planned or estimated prosthetic gap configuration of a resected joint, including a prosthetic gap dimension as well as the designed or estimated resected surface angular alignments.

In various embodiments, method 700 can further comprise coupling the first reference spacer plate to the spacer body (step 730), and optionally coupling the second reference spacer plate to the spacer body (735), to produce a first assembled reference spacer system. In various embodiments, coupling the first and/or second reference spacer plate to the spacer body can comprise slidably engaging each reference spacer plate to the spacer body, with each spacer plate engaged to a side of the spacer body selected to produce an appropriate configuration with respect to the position of the offset elongated handle for insertion in a knee joint of a right or left leg and with respect to the reference spacer plates having the desired predetermined slopes being appropriately located on the superior and/or inferior sides of the spacer body. For example, in a left knee resection with a neutral (0° posterior anterior-posterior slope) distal femoral resection angle and a 7° tibial resection posterior slope, the reference spacer support is positioned with the elongated handle offset to the left of the spacer body, a 7° anterior-posterior angled first reference spacer plate is selected and assembled to the inferior side of the spacer body, and a 0° anterior-posterior angle second reference spacer plate may optionally be assembled to the superior side of the spacer body. Any of a variety of permutations of combinations of reference spacer plates offering various anterior-posterior angles may be selected, with the assembled reference system likewise offering different overall thicknesses based on the selected spacer body and spacer plate thicknesses.

In various embodiments, method 700 can further comprise contacting the first assembled reference spacer system to a resected joint (step 740). Contacting the first assembled reference spacer system to a resected joint can comprise inserting the system into a joint space and positioning the joint to approximate the joint position that a prosthetic device to be implanted will encounter. In various embodiments, contacting the first assembled reference spacer system to a resected joint can comprise contacting one or more contact surfaces of the first assembled reference spacer system with one or more resected surfaces of a joint.

For example, contacting the first assembled reference spacer system to a resected knee joint can comprise contacting a resected femoral surface, such as a resected distal femoral surface or a resected posterior femoral surface, and/or a resected proximal tibial surface, with one or more contact surfaces of the reference spacer system. In various embodiments, contacting a resected joint can further comprise adjusting one or more of the anterior-posterior and angular positions of the first assembled reference system to ensure accurate assessment of the resected joint condition. For example, in various embodiments, the angular position of the first assembled reference spacer system in a knee joint space may be adjusted to ensure that the system is properly aligned with respect to a mechanical axis of the leg (e.g., that axis C-C' is substantially perpendicular to a mechanical axis of the leg) to ensure that evaluation of the angular alignment of the resected joint surfaces may be properly evaluated. Likewise, the anterior-posterior position of the system must be properly located within the joint space to ensure that the prosthetic gap dimension is evaluated at the correct anterior-posterior position in the joint.

Figure 8A:
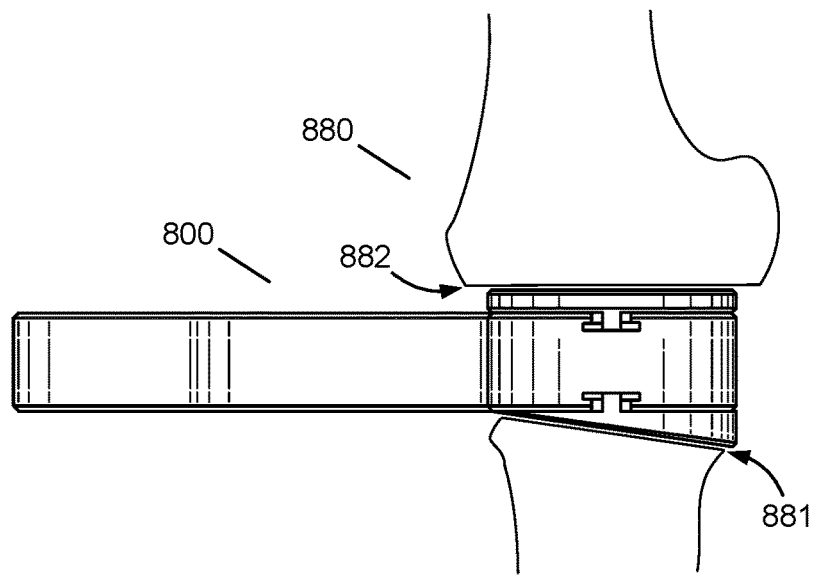
FIG. 8A illustrates a lateral view of an assembled reference spacer system according to various embodiments of the present disclosure inserted in an extension gap of a resected knee joint.
Figure 8B:
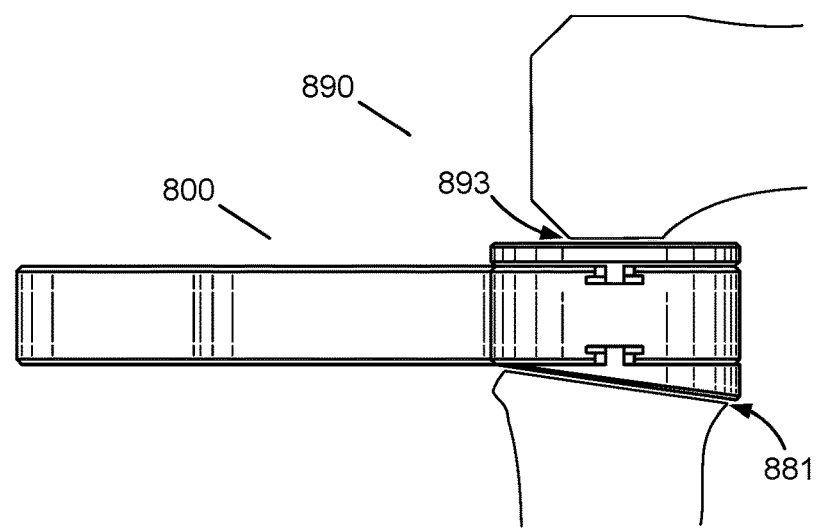
FIG. 8B illustrates a lateral view of an assembled reference spacer system according to various embodiments of the present disclosure inserted in a flexion gap of a resected knee joint.

Moreover, the system operator may further ensure that the orientation of the joint itself is appropriate for optimal assessment of the prosthetic gap in contacting step 740, including, for example, positioning the leg in extension for evaluation of the extension gap (i.e., the prosthetic gap between the resected proximal tibial surface and the resected distal femoral surface) and positioning the leg in flexion for evaluation of the flexion gap (i.e., the prosthetic gap between the resected proximal tibial surface and the resected posterior femoral surface). Likewise, positioning the leg can further include tensioning the ligamentous structures adjacent to the joint to assess the prosthetic gap symmetry in subsequent steps. This can be achieved by the operator's manual application of varus and/or valgus stress to the knee with the assembled reference system inserted into the prosthetic gap (in either extension or in flexion). FIG. 8A illustrates a lateral view of an assembled reference system 800 inserted in an extension gap of a resected knee joint 880 comprising a resected proximal tibial surface 881 and resected distal femoral surface 882. FIG. 8B illustrates a lateral view of assembled reference system 800 inserted in a flexion gap of a resected knee joint comprising resected proximal tibial surface 881 and resected posterior femoral surface 893.

Any of the various positioning activities described above can be included within the meaning of the step of contacting the first assembled reference spacer system to a resected knee joint (step 740), as used herein.

Following contacting step 740, method 700 can further comprise assessing the first assembled reference system fit in the prosthetic gap (step 750). Assessing the first assembled reference system fit in the prosthetic gap can comprise visual and/or tactile evaluation of the fit and/or alignment of first assembled reference system with reference to the resected femoral and tibial surfaces, such as the extension gap comprising resected proximal tibial surface 881 and resected distal femoral surface 882 shown in FIG.

8A, or the flexion gap resected proximal tibial surface 881 and resected posterior femoral surface 893 shown in FIG. 8B. In various embodiments, assessing the first assembled reference system fit in the prosthetic gap can comprise determining one of a precise fit condition, a binding condition, an excessive free movement condition, a symmetry condition, an asymmetry condition, a tibial resection posterior slope congruity condition, a tibial resection posterior slope incongruity condition, a distal femoral resection angle congruity condition, and a distal femoral resection angle incongruity condition. For example, in various embodiments, assessing the first assembled reference system fit in the prosthetic gap can comprise assessing a prosthetic gap dimension, a prosthetic gap symmetry (i.e., gap balance), a tibial resection posterior slope, and/or a distal femoral resection angle relative to the first assembled reference system. Based on a determination of one or more of the above-listed conditions, the reference system may be removed and reconfigured for a second assessment with a second assembled reference system, or a prosthetic gap configuration may be confirmed and/or a complementary prosthetic device selected.

In various embodiments, if one or more of a binding condition, an excessive free movement condition, a tibial resection posterior slope incongruity condition, and a distal femoral resection angle incongruity condition are determined, method 700 can further comprise one of substitute a second spacer body for the first spacer body and substituting a reference spacer plate for one of the first and second reference spacer plates. For example, in response to determining one of a binding condition or an excessive free movement condition, a method can further comprise substituting a second spacer body that is thinner or thicker, respectively. Likewise, in response to determining an incongruity condition, a method can comprise substituting a second reference spacer plate for a first reference spacer plate or substituting a third reference spacer plate for one of a first or second reference spacer plate. In various embodiments, a method can also comprise performing further resection to take more bone or to alter a tibial resection posterior slope or a distal femoral resection angle of a previously resected surface. In various embodiments, various steps of method 700 may be repeated until a precise fit condition, as illustrated in in FIG. 8A or 8B, is determined. The prosthetic gap of a resected joint, including the prosthetic gap dimension and symmetry, as well as the angular alignments of the resected bone surfaces comprising the joint, can thus be established based on the overall thickness of the assembled reference system and the anterior-posterior angles of the reference spacer plates assembled in the reference system used to establish the precise fit condition.

Benefits, other advantages, and solutions to problems have been described herein with regard to specific embodiments. While the systems and methods are described in the context of a knee arthroplasty procedure, the systems and/or their components and methods can similarly be used in other types of medical procedures, including but not limited to ankle, wrist, shoulder, and hip replacement procedures. However, the benefits, advantages, solutions to problems, and any elements that may cause any benefit, advantage, or solution to occur or become more pronounced are not to be construed as critical, required, or essential features or elements of the disclosure. Reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural and functional equivalents to the elements of the above-described embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system comprising:
   a reference spacer support comprising a spacer body and an elongated handle, wherein the spacer body comprises a first side defining a first plane and a second side defining a second plane, wherein the first side and the second side each comprises a spacer body attachment feature, wherein the first plane and the second plane are substantially parallel and define a spacer body thickness, and wherein the spacer body and the elongated handle define a system axis;
   a first reference spacer plate comprising a first contact surface and a first plate attachment feature configured to reversibly engage the spacer body attachment feature; and
   a plate retention device configured to be adjustably attached the spacer body,
   wherein the first reference spacer plate is selected from a plurality of reference spacer plates, and
   wherein the plurality of reference spacer plates is configured to provide a range of predetermined anterior-posterior angles relative to the system axis when each reference spacer plate is engaged to the spacer body.

2. The system of claim 1, further comprising a second reference spacer plate, the second reference spacer plate comprising a second contact surface and a second plate attachment feature configured to reversibly mate to the spacer body attachment feature.

3. The system of claim 2, wherein the spacer body attachment feature comprises a recessed open channel, and wherein one of the first plate attachment feature and the second plate attachment feature comprises an elongate protrusion configured to slidably engage the spacer body attachment feature.

4. The system of claim 3, wherein the recessed open channel comprises an asymmetric cross-section, and wherein the first plate attachment feature and the second plate attachment feature each comprises a corresponding asymmetric protrusion cross-section configured to prohibit engagement of a first plate attachment and second pate attachment in an improper orientation.

5. A kit comprising:
a plurality of spacer bodies, each of the plurality of spacer bodies comprising a spacer body thickness and a spacer body attachment feature;
a plurality of reference spacer plates, each of the plurality of reference spacer plates comprising a reference spacer attachment feature configured to engage the spacer body attachment feature; and
a handle, which is one of configured to removably attach to at least one of the plurality of spacer bodies or is integrally attached to at least one of the plurality of spacer bodies,
wherein an at least one of the plurality of reference spacer plates and an at least one of the plurality of spacer bodies are capable of being manipulated by a user into an assembled condition to produce a reference spacer assembly providing a predetermined reference spacer assembly thickness and a predetermined posterior slope.

6. The kit of claim 5, wherein the handle is integrally attached to a spacer body of the plurality of spacer bodies, and wherein each of the plurality of spacer bodies comprises an integrally attached handle.

7. The kit of claim 5, wherein the predetermined reference spacer assembly thickness comprises a combined thickness of a spacer body and an at least one reference spacer plate.

8. The kit of claim 5, wherein the handle is a modular reference spacer assembly handle configured for removable attachment to each of the plurality of spacer bodies.

9. The kit of claim 5, wherein the plurality of spacer bodies is configured to provide a range of predetermined spacer body thicknesses between about 10 mm and about 20 mm.

10. The kit of claim 9, wherein the kit comprises five spacer bodies having predetermined spacer body thicknesses of about 11 mm, about 13 mm, about 15 mm, about 17 mm, and about 19 mm.

11. The kit of claim 5, wherein the plurality of reference spacer plates is configured to provide a range of predetermined anterior-posterior angles between about 0 degrees and about 10 degrees.

12. The kit of claim 11, wherein the predetermined anterior-posterior angles a about 0 degrees, about 3 degrees, about 5 degrees, and about 7 degrees.

13. A method of assessing a prosthetic gap comprising:
selecting a first spacer body from a plurality of spacer bodies, wherein the first spacer body comprises a first side and a second side opposite the first side;
selecting a first reference spacer plate from a plurality of reference spacer plates, wherein the first reference spacer plate comprises a first contact surface defining a first contact surface plane with a first predetermined posterior slope;
coupling the first reference spacer plate to one of the first side or the second side to produce a first assembled reference spacer system comprising a first predetermined reference spacer thickness;
contacting the first assembled reference spacer system to one a resected femoral surface and a resected proximal tibial surface in a prepared patient knee;
assessing at least one of a prosthetic gap dimension, a prosthetic gap symmetry, a tibial resection posterior slope, and a distal femoral resection angle relative to the first assembled reference spacer system to determine at least one of a precise fit condition, a binding condition, an excessive free movement condition, a symmetry condition, an asymmetry condition, a tibial resection posterior slope congruity condition, a tibial resection posterior slope incongruity condition, a distal femoral resection angle congruity condition, and a distal femoral resection angle incongruity condition.

14. The method of claim 13, further comprising selecting a second reference spacer plate from the plurality of reference spacer plates and coupling the second reference spacer plate to the first spacer body.

15. The method of claim 14, further comprising substituting a second spacer body for the first spacer body in response to determining one of a binding condition or an excessive free movement condition.

16. The method of claim 14, further comprising substituting a third reference spacer plate for one of the first reference spacer plate and the second reference spacer plate in response to determining one of a tibial resection posterior slope incongruity and a distal femoral resection angle incongruity.

17. The method of claim 13, the resected femoral surface comprises a resected distal femoral surface, and wherein the method further comprises positioning the prepared patient knee in a substantially full extension position.

18. The method of claim 13, wherein the resected femoral surface comprises a resected posterior femoral surface, and wherein the method further comprises positioning the prepared patient knee in a substantially 90 degree flexion position.

19. A kit, comprising:
a plurality of spacer bodies, each of the plurality of spacer bodies comprising a spacer body thickness and a spacer body attachment feature, wherein the plurality of spacer bodies is configured to provide a range of predetermined spacer body thicknesses between about 10 mm and about 20 mm; and
a plurality of reference spacer plates, each of the plurality of reference spacer plates comprising a reference spacer plate attachment feature configured to engage the spacer body attachment feature;
wherein an at least one of the plurality of reference spacer plates and at an least one of the plurality of spacer bodies are capable of being manipulated by a user into an assembled condition to produce a reference spacer assembly providing a predetermined reference spacer assembly thickness and a predetermined posterior slope.

* * * * *